United States Patent
Peng et al.

(10) Patent No.: US 11,526,983 B2
(45) Date of Patent: Dec. 13, 2022

(54) IMAGE FEATURE RECOGNITION METHOD AND APPARATUS, STORAGE MEDIUM, AND ELECTRONIC APPARATUS

(71) Applicant: Tencent Technology (Shenzhen) Company Limited, Shenzhen (CN)

(72) Inventors: Pai Peng, Shenzhen (CN); Xinyang Jiang, Shenzhen (CN); Xiaowei Guo, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 27 days.

(21) Appl. No.: 16/856,739

(22) Filed: Apr. 23, 2020

(65) Prior Publication Data

US 2020/0250821 A1    Aug. 6, 2020

Related U.S. Application Data

(63) Continuation of application No. PCT/CN2018/115168, filed on Nov. 13, 2018.

(51) Int. Cl.
  G06K 9/62      (2022.01)
  G06T 7/00      (2017.01)
  G06N 3/08      (2006.01)

(52) U.S. Cl.
  CPC .......... *G06T 7/0012* (2013.01); *G06K 9/6256* (2013.01); *G06N 3/08* (2013.01); *G06T 2207/20081* (2013.01)

(58) Field of Classification Search
  None
  See application file for complete search history.

(56) References Cited

U.S. PATENT DOCUMENTS

2016/0292856 A1    10/2016  Niemeijer et al.
2018/0240017 A1*   8/2018   Huszar ................. G06N 3/08
(Continued)

FOREIGN PATENT DOCUMENTS

CN    105528595 A    4/2016
CN    105989352 A    10/2016
(Continued)

OTHER PUBLICATIONS

Pratt, Harry, et al. "Convolutional neural networks for diabetic retinopathy." Procedia computer science 90 (2016): 200-205. (Year: 2016).*

(Continued)

*Primary Examiner* — Sean M Conner
(74) *Attorney, Agent, or Firm* — Morgan, Lewis & Bockius LLP

(57) ABSTRACT

This application discloses an image feature recognition method performed at a computing device. The computing device obtains a first neural network model by training parameters in a second neural network model using a first training set and a second training set consecutively, image features of training pictures in the first training set being marked and image features of training pictures in the second training set being not marked. After obtaining a first neural network model, the computing device obtains a recognition request for recognizing an image feature in a target picture. The computing device then recognizes the image feature in the target picture by applying the target picture to the first neural network model. Finally the computing device returns a first recognition result of the first neural network model, the first recognition result indicating an image feature (for example, a pathological feature) recognized in the target picture.

20 Claims, 6 Drawing Sheets

(56) References Cited

U.S. PATENT DOCUMENTS

2018/0322371 A1* 11/2018 Dupont De Dinechin ................. G06K 9/6255
2020/0211235 A1* 7/2020 Hsu ...................... G06K 9/0061

FOREIGN PATENT DOCUMENTS

| CN | 106203298 A | * | 12/2016 |
| CN | 106203298 A | | 12/2016 |
| CN | 106897738 A | | 6/2017 |
| CN | 107145903 A | | 9/2017 |
| CN | 107203778 A | | 9/2017 |
| CN | 108230296 A | | 6/2018 |

OTHER PUBLICATIONS

Saleh, Babak, Ahmed Elgammal, and Jacob Feldman. "The role of typicality in object classification: Improving the generalization capacity of convolutional neural networks." arXiv preprint arXiv:1602.02865 (2016). (Year: 2016).*

Chakraborty, Shayok, et al. "Active batch selection via convex relaxations with guaranteed solution bounds." IEEE transactions on pattern analysis and machine intelligence 37.10 (2015): 1945-1958. (Year: 2015).*

Zhou, Zongwei, et al. "Fine-tuning convolutional neural networks for biomedical image analysis: actively and incrementally." Proceedings of the IEEE conference on computer vision and pattern recognition. 2017. (Year: 2017).*

Tencent Technology, ISRWO, PCT/CN2018/115168, Feb. 12, 2019, 7 pgs.

Tencent Technology, IPRP, PCT/CN2018/115168, Jun. 2, 2020, 6 pgs.

* cited by examiner

Positive sample

Negative sample

IMAGE FEATURE RECOGNITION METHOD AND APPARATUS, STORAGE MEDIUM, AND ELECTRONIC APPARATUS

CROSS-REFERENCE TO RELATED APPLICATIONS

This application is a continuation application of PCT Application No. PCT/CN2018/115168, entitled "RECOGNITION METHOD AND DEVICE FOR IMAGE FEATURE, STORAGE MEDIUM AND ELECTRONIC DEVICE" filed on Nov. 13, 2018, which claims priority to Chinese Patent Application No. 201711244421.9, entitled "IMAGE FEATURE RECOGNITION METHOD AND APPARATUS, STORAGE MEDIUM, AND ELECTRONIC APPARATUS" filed with the Chinese National Intellectual Property Administration on Nov. 30, 2017, all of which are incorporated by reference in their entirety.

FIELD OF THE TECHNOLOGY

This application relates to the field of the Internet, and specifically, to an image feature recognition method and apparatus, a storage medium, and an electronic apparatus.

BACKGROUND OF THE DISCLOSURE

Diabetic retinopathy (DR) is an important manifestation in diabetic microangiopathy, is a type of fundus lesion with specific changes, and is one of the severe diabetic complications. DR includes types such as non-proliferative DR (NPDR for short) (or referred to as a simple DR or a background DR) and proliferative DR (PDR for short). As predicted by the World Health Organization (WHO), by 2030, a quantity of global DR patients will increase to 366 million, DR has become one of the four leading blinding eye diseases, and prevention and treatment of the DR will become a serious worldwide problem.

Studies have shown that early diagnosis and treatment on DR patients can effectively prevent loss of vision and blindness, and fundus photography examination is a key to prevention and treatment, regular follow-up to find disease progression, and timely laser intervention for treatment. However, currently, over 50% diabetes patients in the world do not undergo ocular examination in any form, and screening for DR based on a fundus image basically relies on visual observation by an ophthalmologist.

In a case of mass screening, doctors need to analyze and process a quite large volume of data. The manual interpretation method is time-consuming and laborious, and manual screening is impracticable. Moreover, manual screening is strongly subjective, data analysis is complex and is difficult to quantify, and it is difficult to achieve quantitative follow-up.

For a technical problem of low efficiency of screening for DR in the related art, no effective solution has been provided yet.

SUMMARY

Embodiments of this application provide an image feature recognition method and apparatus, a storage medium, and an electronic apparatus, to resolve at least a technical problem of low efficiency of screening for DR in the related art.

According to an aspect of the embodiments of this application, an image feature recognition method is performed at a computing device. The method includes: obtaining a first training set and a second neural network model, image features of training pictures in the first training set being marked and the second neural network model including parameters to be trained; training the parameters of the second neural network model into a first neural network model using the image features of training pictures in the first training set that have been marked; applying a second training set to the first neural network model, image features of training pictures in the second training set being not marked, to recognize image features of a subset of the training pictures in the second training set and marks the image features of the subset of the training pictures in the second training set accordingly; and updating parameters of the first neural network model using the image features of the subset of the training pictures in the second training set that have been marked.

According to another aspect of the embodiments of this application, a non-transitory computer readable storage medium is further provided. The storage medium stores a plurality of program units that, when executed by a computing device having one or more processors, cause the computing device to perform the foregoing image feature recognition method.

According to another aspect of the embodiments of this application, a computing device is further provided. The computing device includes one or more processors and one or more memories storing program units that, when executed by the one or more processors, cause the computing device to perform the foregoing image feature recognition method.

In the embodiments of this application, the server recognizes an image feature in a target picture by using a first neural network model when a recognition request is obtained, and returns a first recognition result of the first neural network model, the first recognition result being used for at least indicating an image feature (for example, a pathological feature) recognized from the target picture. The foregoing neural network model may exist in a computer device in a form of software, and rapidly show a recognition result. If a to-be-recognized pathological feature is DR, a technical problem of low efficiency of screening for DR in the related art may be resolved, thereby improving efficiency of screening for DR.

BRIEF DESCRIPTION OF THE DRAWINGS

The accompanying drawings described herein are used for providing further understanding for this application and constitute a part of this application. Exemplary embodiments of this application and descriptions thereof are used for explaining this application and do not constitute an improper limitation to this application. In the accompanying drawings.

DESCRIPTION OF EMBODIMENTS

To make a person skilled in the art better understand solutions of this application, the following clearly and completely describes the technical solutions in the embodiments of this application with reference to the accompanying drawings in the embodiments of this application. Apparently, the described embodiments are merely some rather than all of the embodiments of this application. All other embodiments obtained by a person skilled in the art based on the embodiments of this application without creative efforts shall fall within the protection scope of this application.

In the specification, claims, and accompanying drawings of this application, the terms "first", "second", and so on are intended to distinguish between similar objects rather than indicating a specific order. It is understood that the data termed in such a way are interchangeable in proper circumstances, so that the embodiments of this application described herein can be implemented in other orders than the order illustrated or described herein. Moreover, the terms "include", "have" and any other variants mean to cover the non-exclusive inclusion, for example, a process, method, system, product, or device that includes a list of steps or units is not necessarily limited to those expressly listed steps or units, but may include other steps or units not expressly listed or inherent to such a process, method, product, or device.

According to a first aspect of the embodiments of this application, a method embodiment of an image feature recognition method is provided.

Figure 1:
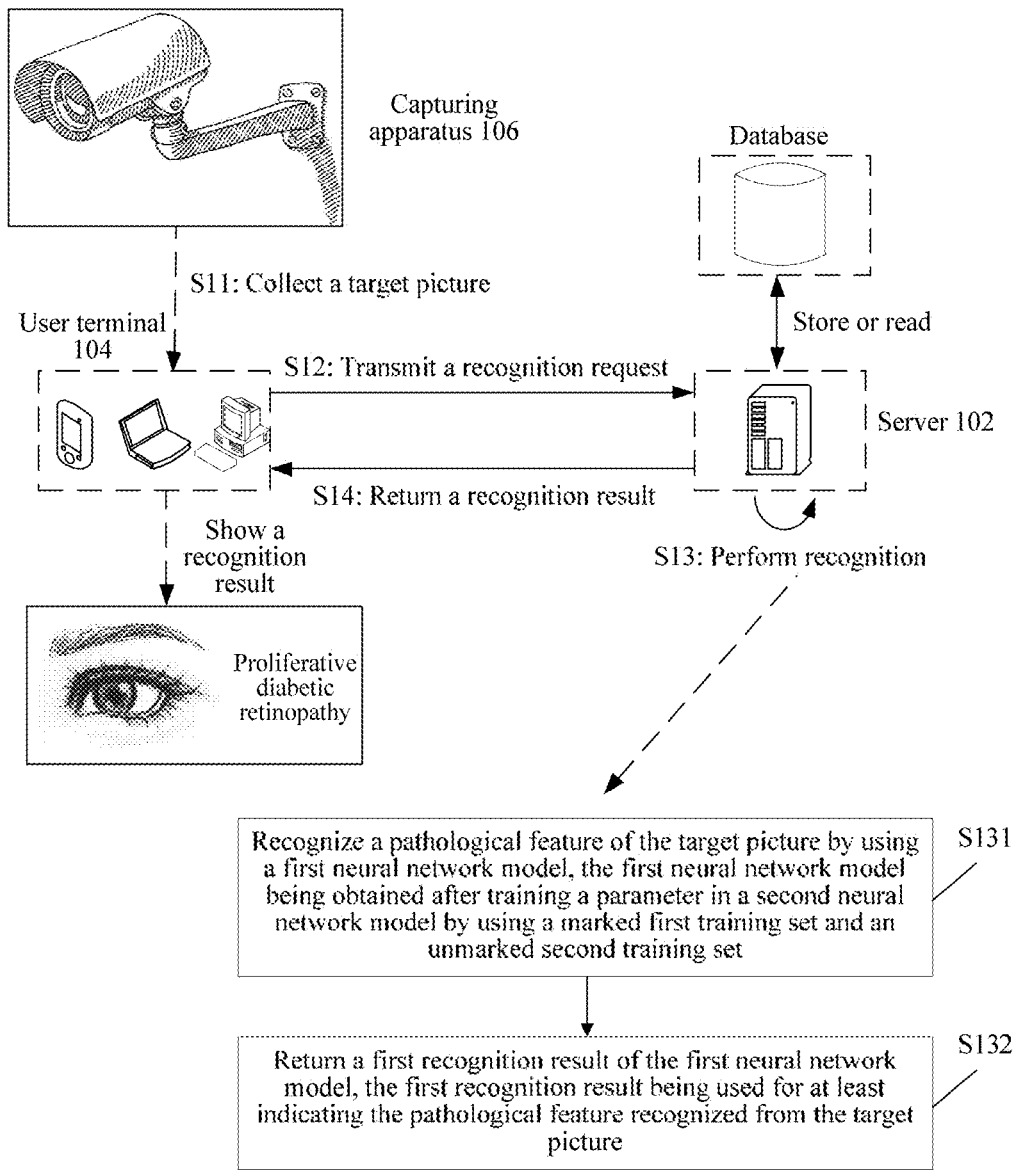
FIG. 1 is a schematic diagram of a hardware environment of an image feature recognition method according to an embodiment of this application.

Optionally, in this embodiment, the image feature recognition method may be applied to a hardware environment including a server 102 and a terminal 104 shown in FIG. 1. As shown in FIG. 1, the server 102 is connected to the terminal 104 through a network. The network includes, but is not limited to, a wide area network, a metropolitan area network, or a local area network. The terminal 104 is not limited to a PC, a mobile phone, a tablet computer, and the like. The image feature recognition method in the embodiments of this application may be performed by the server 102, or may be performed by the terminal 104, or may be performed by both the server 102 and the terminal 104. The image feature recognition method in the embodiments of this application performed by the terminal 104 may alternatively be performed by a client installed in the terminal.

The following describes a full procedure including the method of this application in detail by using performing the method of this application on a server as an example:

Step S11: A user terminal 104 captures a picture (that is, a target picture) of a pathological part of a target object by using a capturing apparatus 106.

The capturing apparatus may be an independent image capturing device (for example, a camera, an imager based on a radiation principle), or may be a module integrated on a user terminal.

Step S12: The terminal transmits a recognition request to a server, to request to recognize an image feature in the target picture, for example, to analyze and recognize a condition, for example, information such as a pathological part and a disease type, according to an image.

Optionally, the user terminal and the server may be integrated as the same device, or may be two separate and different devices. The two devices may exist in the same local area network and communicate with each other through the local area network; or may exist in different local area networks and communicate with each other through the Internet.

Optionally, the server may exist in a form of a cloud server, and the user terminal may be any terminal, for example, a mobile phone of a user. The user may transmit a pathological image (the target picture) photographed at any time to the cloud server for diagnosis. The server may exist in a hospital as an auxiliary condition diagnosis device, and is a good helper for a doctor to diagnose.

Step S13: Recognize and diagnose the condition according to the target picture. An implementation may be as follows:

Step S131: Recognize the image feature (for example, the pathological feature) in the target picture by using a first neural network model, the first neural network model being obtained after training a parameter in a second neural network model by using a marked first training set and an unmarked second training set, pathological features of training pictures in the first training set being marked, and pathological features of training pictures in the second training set being not marked.

Step S132: Return a first recognition result of the first neural network model, the first recognition result being used for at least indicating the pathological feature recognized from the target picture.

Step S14: The server returns the recognition result to the terminal, for the terminal to represent the recognition result.

Improvements of this application to the full procedure are mainly in step S13 and steps related to step S13, and the improvements are described in detail below with reference to FIG. 2.

Figure 2:
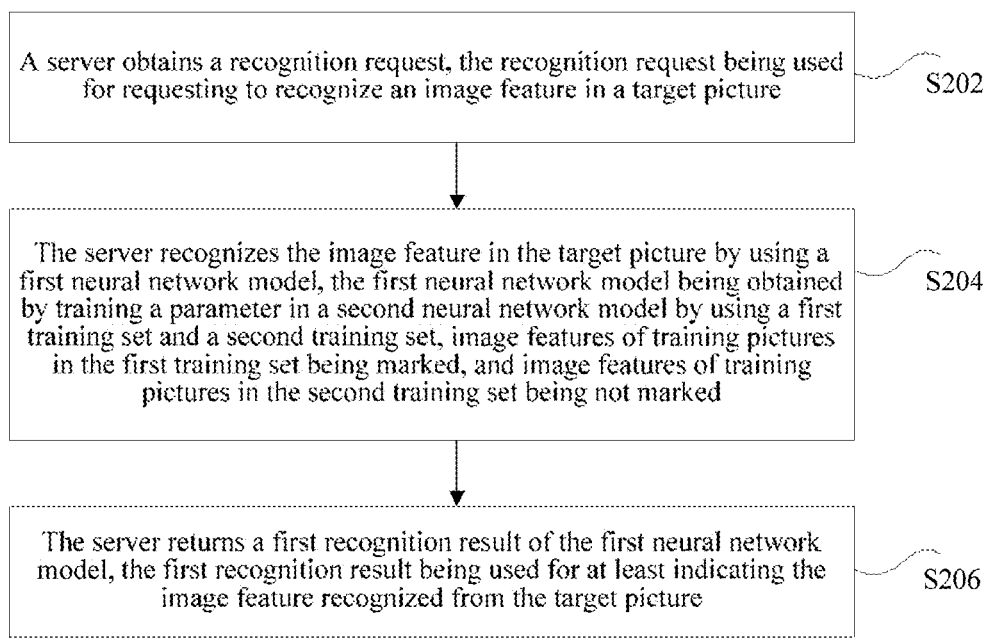
FIG. 2 is a flowchart of an optional image feature recognition method according to an embodiment of this application.

FIG. 2 is a flowchart of an optional image feature recognition method according to an embodiment of this application. As shown in FIG. 2, the method may include the following steps:

Step S202: A server obtains a recognition request, the recognition request being used for recognizing an image feature in a target picture.

Types of pictures captured by a capturing apparatus include, but are not limited to: a black and white picture or a color picture obtained by photographing, an image obtained by computed tomography, an image obtained by positron emission tomography, an image obtained by magnetic resonance imaging, an image obtained by medical ultrasonography, and the like.

The target picture are captured by photographing a suspected lesion part of a target object. The image feature may be a pathological feature, and the pathological feature is an image feature of the lesion part, for example, a feature having no retinal neovascularization corresponding to a NPDR area, and a feature having retinal neovascularization corresponding to a PDR area.

Step S204: The server recognizes the image feature in the target picture by using a first neural network model, the first neural network model being obtained by training a parameter in a second neural network model by using a first training set and a second training set, image features of training pictures in the first training set being marked, and image features of training pictures in the second training set being not marked; the first neural network model trained by the first training set being used for recognizing the image features of the training pictures in the second training set, and the training pictures with the image features recognized in the second training set being used for continuing to train the first neural network model.

The foregoing second neural network model is a model whose parameter is not initialized (for example, a deep neural network model). First, the second neural network model is trained by using the marked training pictures in the first training set, to initialize the parameter of the second neural network model, and the parameter is optimized by using the unmarked training pictures in the second training set; and then the foregoing first neural network model is obtained.

If the second neural network model is trained by completely using marked training pictures, marking the training pictures is highly time-consuming because of a relatively large quantity of demanded training pictures. However, in the technical solutions of this application, only some training pictures may be marked (that is, pictures in the first training set), and the remaining training pictures are not marked, thereby reducing a workload during model training.

Step S206: The server returns a first recognition result of the first neural network model, the first recognition result being used for at least indicating the image feature recognized from the target picture.

The recognition result herein is closely related to the training of the neural network model. For example, if the training pictures include positive and negative sample pictures of various types of DR, then the recognition result is a specific type of DR or several types of DR, and a specific type of DR corresponds to a corresponding pathological feature (for example, the NPDR corresponds to having no retinal neovascularization, and the PDR corresponds to having retinal neovascularization). For another example, if the training pictures include positive and negative sample pictures of various types of pneumonia, then the recognition result is a type of pneumonia or several types of pneumonia. The training pictures may alternatively be positive and negative sample pictures of other pathological types, and details are not described herein again.

Through step S202 to step S206, the server recognizes the image feature in the target picture by using a first neural network model in a case of obtaining the recognition request, and returns a first recognition result of the first neural network model, the first recognition result being used for at least indicating the image feature recognized from the target picture. The foregoing neural network model may exist in a computer device in a form of software, and rapidly show a recognition result. If a to-be-recognized image feature (for example, a pathological feature) is DR, a technical problem of low efficiency of screening for DR in the related art may be resolved, thereby improving efficiency of screening for DR.

This embodiment of this application is further described below in detail with reference to steps shown in FIG. 2.

In the technical solutions provided in step S202, a server obtains a recognition request, the recognition request being used for requesting to recognize an image feature in a target picture.

Figure 3:
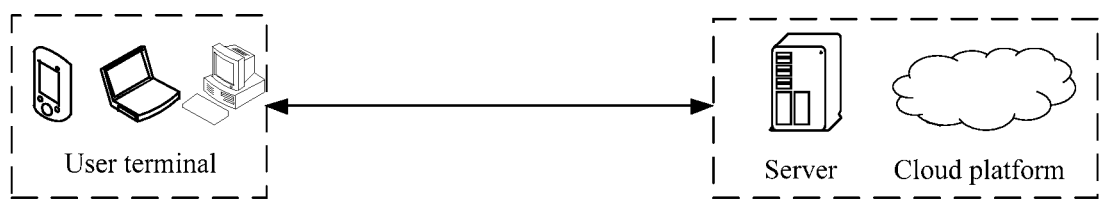
FIG. 3 is a schematic diagram of a hardware environment of an optional image feature recognition method according to an embodiment of this application.

The method of this application may be applied to scenarios such as a hospital server, an Internet cloud platform, and a local area network. The terminal transmitting the recognition request may directly be a terminal of the foregoing hospital server, a terminal of the Internet cloud platform, or the terminal in the local area network, or may be a device communicably connected to the hospital server, the Internet cloud platform, or the local area network. For example:

As shown in FIG. 3, the foregoing terminal may be a user terminal with a camera such as a mobile phone, a tablet computer, or a notebook computer. The user terminal may initiate the recognition request by transmitting a target picture that meets requirements (for example, definition requirements, image size requirements, and photographing a specified part) to the hospital server, the Internet cloud platform, and the like.

Figure 4:
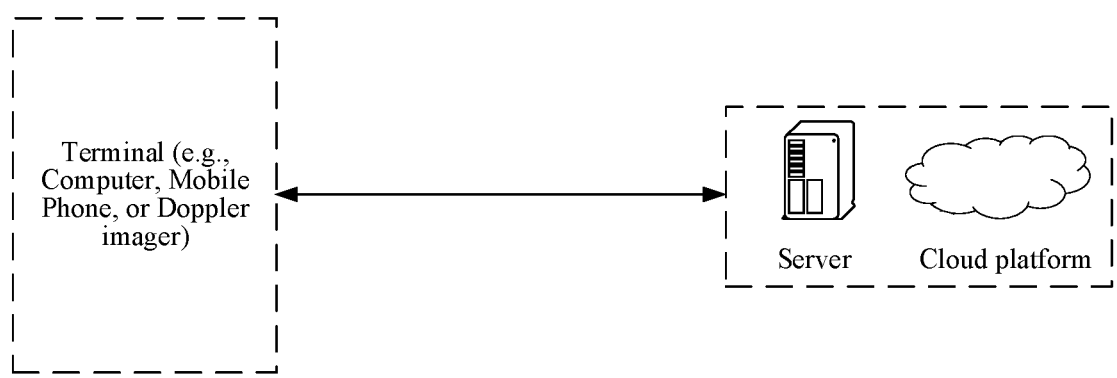
FIG. 4 is a schematic diagram of a hardware environment of an optional image feature recognition method according to an embodiment of this application.

As shown in FIG. 4, the foregoing terminal may be another device in the hospital (for example, a computer, a mobile phone, or a Doppler imager used by medical staff) that can be communicably connected to the foregoing hospital server or the Internet cloud platform. The hospital server or the Internet cloud platform may provide services for all doctors in one or more hospitals. A doctor transmits, by using the foregoing device, a target picture to the hospital server or the Internet cloud platform to initiate a recognition request, and then a recognition result is returned to assist the doctors to diagnose.

Figure 5:
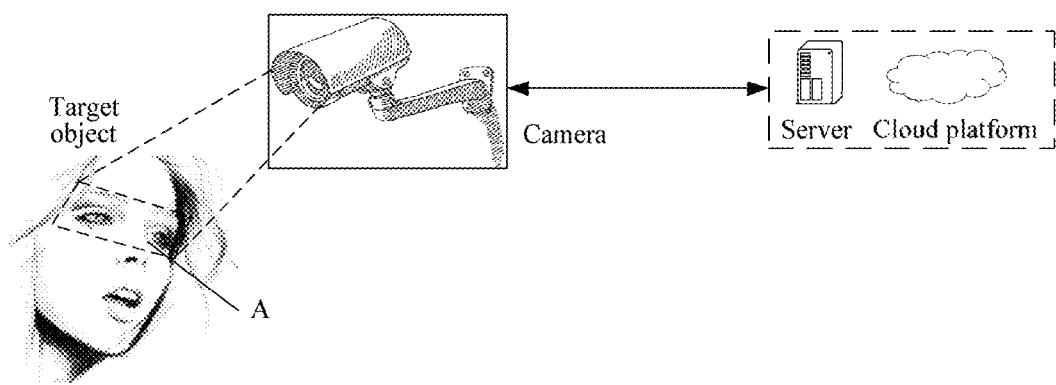
FIG. 5 is a schematic diagram of a hardware environment of an optional image feature recognition method according to an embodiment of this application.

As shown in FIG. 5, the foregoing terminal may be a camera in a public space and can be communicably connected to the foregoing hospital server or the Internet cloud platform. The camera photographs a specified part (for example, an area at which the eyes are located) of a crowd (that is, a target object) in real time, and transmits a target picture obtained by photographing to the hospital server or the Internet cloud platform to initiate a recognition request.

For the third case, rapid diagnosis can be provided for some epidemic diseases, a patient in a public space can be located quickly, and a specific prompt is also provided (to prompt the patient), to produce a good effect of inhibiting spreading of the diseases.

The recognition result in this application corresponds to the first neural network model, that is, the first neural network model is obtained by training with images of a specific type of pathology, so that the first neural network model can recognize such type of pathology.

Figure 6:
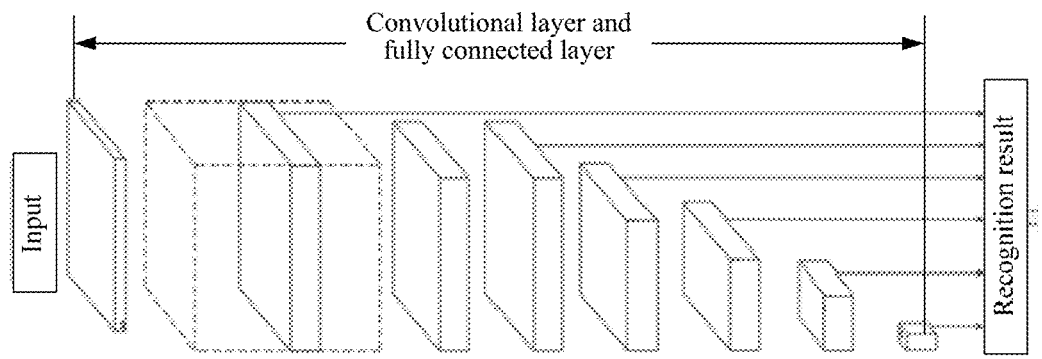
FIG. 6 is a schematic diagram of an optional neural network model according to an embodiment of this application.

Optionally, the first neural network model can be trained with images of several types of pathology, so that the first neural network model is enabled to recognize the several types of pathology. An optional neural network model is shown in FIG. 6, including an input layer, a plurality of convolutional layers and fully connected layers, and an output layer outputting a recognition result.

In the technical solutions provided in step S204, the server recognizes an image feature in a target picture by using a first neural network model, the first neural network model being obtained by training a parameter (which may be a fitting parameter in the plurality of convolutional layers and fully connected layers) in a second neural network model by using a first training set and a second training set, image features of training pictures in the first training set being marked, and image features of training pictures in the second training set being not marked.

The first neural network model trained by the first training set is used for recognizing the image features of the training pictures in the second training set, and the training pictures with the image features recognized in the second training set is used for continuing to train the first neural network model.

Optionally, before the server recognizes the image feature in the target picture by using a first neural network model, the server can train the first neural network model in advance: training the second neural network model by using the training pictures in the first training set and the training pictures in the second training set sequentially, and using the trained second neural network model as the first neural network model, the training pictures in the second training set used for training the second neural network model being marked by using the image features that are recognized by the second neural network model in advance.

In the foregoing embodiments, the training, by the server, the second neural network model by using the training pictures in the first training set and the training pictures in the second training set sequentially, and using the trained second neural network model as the first neural network model can be implemented in the following manner.

Step S21: Perform training initialization on the parameter in the second neural network model by using the training pictures in the first training set, and use the second neural network model after the parameter initialization as a third neural network model.

Figure 7:
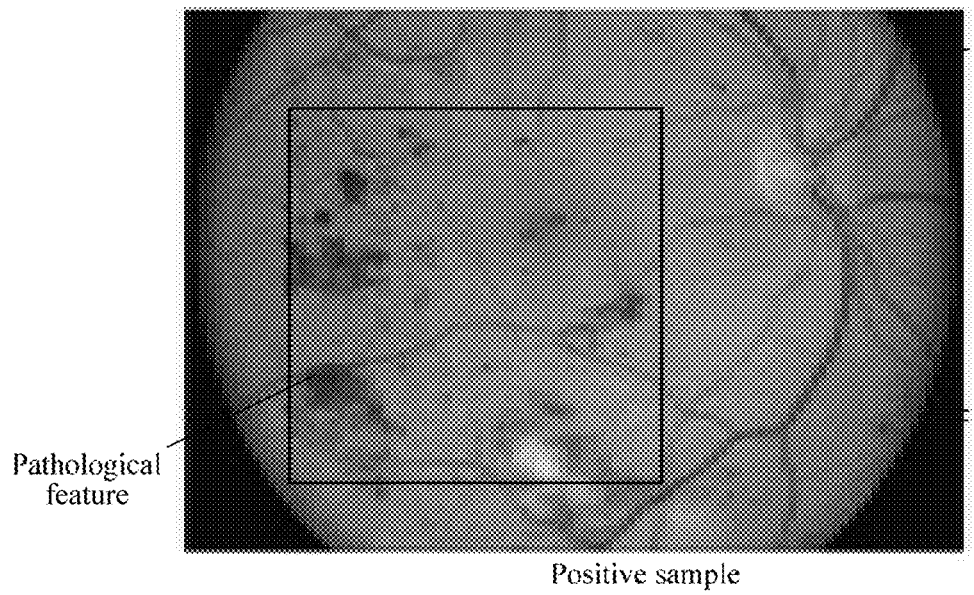
FIG. 7 is a schematic diagram of an optional positive sample image according to an embodiment of this application.
Figure 8:
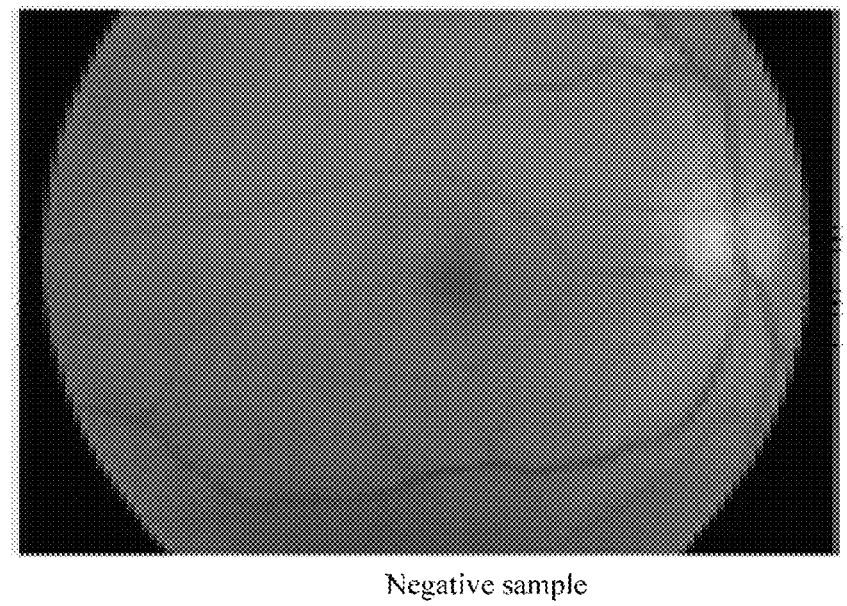
FIG. 8 is a schematic diagram of an optional negative sample image according to an embodiment of this application.

The first training set may include a training picture of a positive sample and a training picture of a negative sample. An image area at which a pathological feature is located and a pathological type of the pathological feature are recognized in the training picture of the positive sample. A specific image area not including a pathological feature is recognized from the training picture of the negative sample. An optional positive sample image is shown in FIG. 7, and an optional negative sample image is shown in FIG. 8.

For example, for DR, two pathological types, namely, NPDR and PDR, can be recognized. The second neural network model can learn of related image features (image features such as wavelet features and textural features) of the two pathological types, namely, NPDR and PDR, from the positive and negative samples. Whether retinal neovascularization occurs may be used as a sign. For example, it can be learned that there is no retinal neovascularization (which can be recognized by using the foregoing image features) in NPDR (or referred to as a simple DR or a background DR), and there is retinal neovascularization in the PDR.

Optionally, the foregoing pathological types may be divided according to requirements. For example, PDR may be sub-divided into mild NPDR, moderate NPDR, severe NPDR, and PDR; and NPDR and other diseases may be also sub-divided in a similar manner.

Step S22: Recognize, the image features of the training pictures in the second training set by using the third neural network model, and mark the training pictures in the second training set by using second recognition results of the third neural network model, the second recognition results are used for at least indicating the image features recognized from the training pictures in the second training set.

A sample size of training pictures in the first training set is limited, so that the training effect is unlikely to be good (for example, the parameter in the second neural network model is in under-fitting, rather than an optimal value) if the second neural network model is trained by using only the samples in the first training set. However, increasing the sample size in the first training set will greatly increase the workload of manual marking (marking the training pictures), and the loss outweighs the gain.

To resolve the foregoing problems, a novel training method is provided in this application. The samples are divided into the first training set and the second training set, after training initialization (which equals to preliminary training) is performed on the parameter in the second neural network model by using training pictures in the first training set, the second neural network model has a preliminary recognition capability (which can recognize some image features in images with obvious image features), and image features (that is, pathological features) of training pictures in the second training set are recognized by using the second neural network model having the preliminary recognition capability.

Optionally, the marking the training pictures in the second training set by using second recognition results of the third neural network model may include: searching all the second recognition results of the training pictures in the second training set for a plurality of third recognition results with a highest confidence; and marking corresponding training pictures in the second training set by using the third recognition results.

The second recognition results may further be used for indicating probabilities that the recognized image features belong to each of a plurality of pathological types, and searching all the second recognition results of the training pictures in the second training set for a plurality of (for example, N) third recognition results with a highest confidence may be implemented in the following manner.

Step S221: Calculate a confidence s of a second recognition result of a current training picture in the second training set according to the following formula:

$$s = PA * d^{w_1} + w_2 * v$$

PA is a parameter that is used for representing importance of the current training picture and that is determined according to a probability of each type in the second recognition result of the current training picture, d being a density parameter determined according to a feature vector recognized by the third neural network model from the current training picture and a feature vector of the training pictures in the second training set, v being a diversity parameter determined according to the feature vector recognized by the third neural network model from the current training picture and a feature vector of the training pictures in the first training set, $w_1$ and $w_2$ being pre-configured parameters.

An optional calculation formula of PA is as follows:

$$PA = -\sum_{i=1}^{N_c} p_i \log(p_i)$$

$p_i$ represents a probability of belonging to the $i^{th}$ type in $N_c$ types, and a value of i ranges from 1 to $N_c$.

An optional calculation formula of d is as follows:

$$d = \frac{1}{|M1|} \sum_{x'=1}^{M1} \frac{f_{FC}(x) f_{FC}(x')}{\|f_{FC}(x)\| * \|f_{FC}(x')\|}$$

A feature vector $f_{FC}$ of a fully connected layer (that is, the fully connected layer adjacent to the output layer, or referred to as a classification layer, in FIG. 6) of a previous layer of an image classification layer in a second training set U, a density x, and a mean cosine distance of a feature vector corresponding to images in the second training set U may be extracted by using a classification model. In the formula, $f_{FC}(x)$ represents a feature vector of a current training picture, $f_{FC}(x')$ represents a feature vector of training pictures in U, M1 represents a quantity of training pictures in the second training set U, an operator "$\|f_{FC}(x)\|$" represents a norm of the vector $f_{FC}(x)$, and $\|f_{FC}(x')\|$ represents a norm of the vector $f_{FC}(x')$ which is actually a mapping from a normed linear space to a non-negative real number. If $f_{FC}(x)$ is a two-dimensional vector, the "$\|f_{FC}(x)\|$" represents a length of the vector $f_{FC}(x)$.

Optionally, the images in U may be clustered according to the feature vector of the fully connected layer by using the K-means algorithm, to obtain K cluster centers. Because any image x in U is clustered, the foregoing $f_{FC}(x')$ may be replaced with a feature vector of the cluster centers. In this case, M1 is a quantity K of the cluster centers (or clusters). A total quantity of calculations can be greatly reduced by using such a method.

An optional calculation formula of v is as follows:

$$v = -\frac{1}{|M2|} \sum_{x'=1}^{M2} \frac{f_{FC}(x) f_{FC}(x')}{\|f_{FC}(x)\| * \|f_{FC}(x')\|}$$

A feature vector $f_{FC}$ of a fully connected layer (that is, the fully connected layer adjacent to the output layer, or referred to as a classification layer in FIG. 6) of a previous layer of an image classification layer in a first training set V, a density x, and a mean cosine distance of a feature vector corresponding to an image in the first training set V may be extracted by using the classification model. In the formula, $f_{FC}(x)$ represents a feature vector of a current training picture, $f_{FC}(x')$ represents a feature vector of training pictures in V, and M2 represents a quantity of training pictures in the first training set V.

Optionally, the images in V may be clustered according to the feature vector of the fully connected layer by using the K-means algorithm, to obtain R cluster centers. Because any image x in V is clustered, the foregoing $f_{FC}(x')$ may be replaced with a feature vector of the cluster centers. In this case, M2 is a quantity R of the cluster centers (or clusters). A total quantity of calculations can be greatly reduced by using such a method.

Step S222: Obtain a plurality of results with a highest confidence in all the second recognition results of the training pictures in the second training set as third recognition results.

In addition to uncertainty, density, and diversity, evaluation indexes of an importance score (the confidence) may be another index of the same class, for example, a gradient length and a Fisher information matrix. In addition to measurement based on each picture, the evaluation indexes may further be used for measurement based on an image set after data enhancement is performed on each picture.

Step S23: Re-adjust a parameter in the third neural network model by continuing to train the third neural network model by using the marked training pictures in the second training set, and use the third neural network model after the parameter re-adjustment as the first neural network model.

In the technical solution provided in step S206, the server returns a first recognition result of the first neural network model, the first recognition result being used for at least indicating the image feature recognized from the target picture.

Optionally, the returning a first recognition result of the first neural network model may include: returning a first recognition result used for representing NPDR; and/or returning a first recognition result used for representing PDR.

Application modes of the technical solutions of this application on a product side include, but are not limited to, foreground recognition and background recognition. For example, business logic is that a fundus picture of a to-be-predicted patient is transferred to a server on which the technical solutions of this application are located for disease classification, and returns a severity degree of the disease (for example, normal, mild non-proliferative, moderate non-proliferative, severe non-proliferative, or proliferative) according to a classification result. Such solutions may be directed to a hospital and a private doctor for auxiliary diagnose on DR, or may be directed to an individual to help the individual for health consultation.

By using the recognition solutions of this application, a rate of convergence of a disease diagnosis model (for example, a DR classification model) can be accelerated, when a same volume of data is marked, a degree of convergence is improved greatly, and costs of manual marking are reduced, and when a classification model with the same quality is trained, the volume of data that needs to be manually marked is reduced greatly by using a frame of this application.

In an optional embodiment, details are provided below by using DR as an example.

In this optional embodiment, when a deep neural network model is trained, the following steps may be cycled until a model converges:

providing an unmarked data set U (the second training set), a marked data set L (the first training set), and a DR classification model f (that is, the second neural network model), and training f on the marked data L; predicting data in the unmarked data set U by using f; quantitatively calculating the uncertainty, the density, and the diversity of the data based on a prediction result to obtain a diversity score (that is, a confidence) of each piece of data in U; and sorting the data in U according to the diversity score, selecting top N pieces of data to mark the top N pieces of data and add the top N pieces of data into L, and further training m.

This embodiment of this application is further described below in detail with reference to optional steps:

Step S31: Input the marked data set L including $N_L$ images, and train the DR classification model f on L.

Step S32: Provide the unmarked data set U including $N_U$ images, and input fundus images (that is, the training pictures) in U into the classification model f to predict a classification result P, where P is a matrix of $N_u * N_c$ (where a value of $N_u$ is a positive integer not greater than a quantity $N_U$ of images), and each dimension in a row vector represents a probability that a current picture belongs to the $N_i^{th}$ ($N_i$ is a constant not greater than a quantity $N_c$ of classes) class predicted by the model.

The $N_c$ classes herein may be the two pathological types, namely, NPDR and PDR, or may be a sub-divided type.

Step S33: Provide a prediction result P of any fundus image in U according to the prediction result of the model f on the unmarked data, and evaluate the importance of each image by using the following three indexes.

(1) Uncertainty PA $$PA = -\sum_{i=1}^{N_c} p_i \log(p_i)$$

$p_i$ represents the probability that the fundus image belongs to the $N_i^{th}$ class, and may be outputted by the model.

(2) Density d

A feature vector of a fully connected layer of a previous layer of an image classification layer of a fundus image in U may be extracted by using the classification model f; and such a feature of the image in U is clustered by using the K-means algorithm, to obtain K cluster centers.

For any fundus image x in U, the density x and a mean cosine distance of a feature vector corresponding to an image in U can be calculated by using the following formula:

$$d = \frac{1}{|M1|} \sum_{x'=1}^{M1} \frac{f_{FC}(x) f_{FC}(x')}{\|f_{FC}(x)\| \|f_{FC}(x')\|}$$

$f_{FC}$ represents a feature of a fully connected layer of the last layer of the extracted image.

(3) Diversity

A feature of a fully connected layer of a last layer of an image in the L is extracted by using the classification model.

Such a feature of the image in the L is clustered by using the K-means algorithm, to obtain K cluster centers.

For any image x in U, the diversity thereof can be calculated by using the following formula:

$$v = -\frac{1}{|M2|} \sum_{x'=1}^{M2} \frac{f_{FC}(x) f_{FC}(x')}{\|f_{FC}(x)\| \|f_{FC}(x')\|}$$

Step S34: Fuse the three indexes by using the following formula to obtain an importance score s (or referred to as a confidence) of each image:

$s = PA * d^{w_1} + w_2 * v$, where $w_1$ and $w_2$ are weights of indexes or preset parameters. For example, $w_1$ is 0.5, $w_2$ is 0.3; $w_1$ is 0.8, $w_2$ is 0.1; or $w_1$ is 0.4, $w_2$ is 0.6. The values may be adjusted according to actual situations.

Step S35: Sort images in U according to s, mark the top N images, and update U.

Step S36: Add the newly marked images into the training set L, and return to step S601 to start a new iteration.

A plurality of iterations may be performed according to requirements, thereby improving recognition accuracy of a neural network model.

After the neural network model is trained, the model may be applied to scenarios shown in FIG. 1, FIG. 3, and FIG. 5. A user captures an image of a pathological part and uploads the image on a mobile terminal, and receives a recognition result returned by the neural network model. For example, a probability of NPDR is 90%, a probability of PDR is 5%, and a probability of overall exclusion is 5%

If a DR fundus image classification model (that is, the first neural network model) is trained by using a supervised learning method, the following defects may be caused:

(1) Performance of the DR classification model depends on a scale of data manually marked, and a classification model with high quality needs to be trained by using a large scale of marked data;

(2) That marking personnel may add newly marked data in a process of training is not considered in the training method of the DR classification model, and only a scenario of performing one-time training in an unchanged training set is considered.

(3) The DR classification model is in short of a mechanism of automatically selecting and providing high-quality and unmarked data for the marking personnel to generate newly training data.

However, in the embodiments of this application, a large quantity of manually marked data with known classification does not need to be used as training samples, data that enables the model to converge at a higher speed can be marked through automatic and purposeful selection, and is used for training of a next stage. By using such a method, a quantity of marked data needed before convergence of model training can be reduced greatly, which effectively reduces the costs caused by manually marking data during training, thereby training a high-quality model with the least marked data.

For simple descriptions, the foregoing method embodiments are stated as a series of action combinations. However, a person skilled in the art needs to know that this application is not limited to the sequence of the described actions because according to this application, some steps may use another sequence or may be simultaneously performed. Secondarily, a person skilled in the art needs to know that the embodiments described in the specification all belong to optional embodiments and the related actions and modules are not necessary for this application.

According to the descriptions in the foregoing implementations, a person skilled in the art may clearly learn that the method according to the foregoing embodiments may be implemented by relying on software and a necessary and commonly used hardware platform or by using hardware, but in many cases the former is a better implementation. Based on such an understanding, the technical solutions of this application essentially or the part contributing to the related art may be implemented in a form of a software product. The computer software product is stored in a storage medium (such as a ROM/RAM, a magnetic disk, or an optical disc) and includes several instructions for instructing a terminal device (which may be a mobile phone, a computer, a server, a network device, or the like) to perform the methods described in the embodiments of this application.

Figure 9:
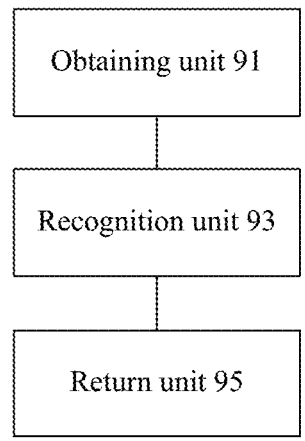
FIG. 9 is a schematic diagram of an optional image feature recognition apparatus according to an embodiment of this application.

According to another aspect of the embodiments of this application, an image feature recognition apparatus configured to implement the foregoing image feature recognition method is further provided. FIG. 9 is a schematic diagram of an optional image feature recognition apparatus according to an embodiment of this application, and the apparatus may be applied to a server. As shown in FIG. 9, the apparatus may include: an obtaining unit 91, a recognition unit 93, and a return unit 95.

The obtaining unit 91 is configured to obtain a recognition request, the recognition request being used for requesting to recognize an image feature in a target picture.

Types of pictures captured by a capturing apparatus include, but are not limited to: a black and white picture or a color picture obtained by photographing, an image obtained by computed tomography, an image obtained by positron emission tomography, an image obtained by magnetic resonance imaging, an image obtained by medical ultrasonography, and the like.

The target picture are captured by photographing a suspected lesion part of a target object. The image feature is a feature of the lesion part, for example, a feature having no retinal neovascularization corresponding to a NPDR area, and a feature having retinal neovascularization corresponding to a PDR area.

The recognition unit 93 is configured to recognize the image feature in the target picture by using a first neural network model, the first neural network model being obtained by training a parameter in a second neural network model by using a first training set and a second training set, image features of training pictures in the first training set being marked, and image features of training pictures in the second training set being not marked.

The first neural network model trained by the first training set is used for recognizing the image features of the training pictures in the second training set, and the training pictures with the image features recognized in the second training set is used for continuing to train the first neural network model.

The foregoing second neural network model is a model whose parameter is not initialized (for example, a deep neural network model). First, the second neural network model is trained by using the marked training pictures in the first training set, to initialize the parameter of the second neural network model, and the parameter is optimized by using the unmarked training pictures in the second training set; and then the foregoing first neural network model is obtained.

If the second neural network model is trained by completely using marked training pictures, marking the training pictures is highly time-consuming because of a relatively large quantity of demanded training pictures. However, in the technical solutions of this application, only some training pictures may be marked (that is, pictures in the first training set), and the remaining training pictures are not marked, thereby reducing a workload during model training.

The return unit 95 is configured to return a first recognition result of the first neural network model, the first recognition result being used for at least indicating the image feature recognized from the target picture.

The recognition result herein is closely related to the training of the neural network model. For example, if the training pictures include positive and negative sample pictures of various types of DR, then the recognition result is a specific type of DR or several types of DR, and a specific type of DR corresponds to a corresponding pathological feature (for example, the NPDR corresponds to having no retinal neovascularization, and the PDR corresponds to having retinal neovascularization). For another example, if the training pictures include positive and negative sample pictures of various types of pneumonia, then the recognition result is a type of pneumonia or several types of pneumonia. The training pictures may alternatively be positive and negative sample pictures of other pathological types, and details are not described herein again.

The obtaining unit 91 in the embodiments may be configured to perform step S202 in this embodiment of this application, the recognition unit 93 in this embodiment may be configured to perform step S204 in the embodiments of this application, and the return unit 95 in the embodiments may be configured to perform step S206 in the embodiments of this application.

Examples and application scenarios in which the foregoing modules are the same as those of the corresponding steps, but are not limited to the content disclosed in the foregoing embodiments. The foregoing modules may be run in the hardware environment shown in FIG. 1 as a part of the apparatus, and may be implemented by software, or may be implemented by hardware.

Through the foregoing modules, the image feature of the target picture is recognized by using the first neural network model when the recognition request is obtained, and a first recognition result of the first neural network model is returned, the first recognition result being used for at least indicating the image feature recognized from the target picture. The foregoing neural network model may exist in a computer device in a form of software, and rapidly show a recognition result. If a to-be-recognized image feature (for example, a pathological feature) is DR, a technical problem of low efficiency of screening for DR in the related art may be resolved, thereby improving efficiency of screening for DR.

Optionally, the apparatus of this application may further include a training unit, configured to, before the image feature is recognized from the target picture by using a first neural network model, train the second neural network model by using the training pictures in the first training set and the training pictures in the second training set sequentially, and use the trained second neural network model as the first neural network model, the training pictures in the second training set used for training the second neural network model being marked by using the image features that are recognized by the second neural network model in advance.

The training unit may include the following modules:

a first training module, configured to perform training initialization on the parameter in the second neural network model by using the training pictures in the first training set, and use the second neural network model after the parameter initialization as a third neural network model;

a recognition and marking module, configured to recognize, the image features of the training pictures in the second training set by using the third neural network model, and mark the training pictures in the second training set by using second recognition results of the third neural network model, the second recognition results being used for at least indicating the image features recognized from the training pictures in the second training set; and a second training module, configured to re-adjust a parameter in the third neural network model by continuing to train the third neural network model by using the marked training pictures in the second training set, and use the third neural network model after the parameter re-adjustment as the first neural network model.

Optionally, the recognition and marking module may include: a searching sub-module, configured to search all the second recognition results of the training pictures in the second training set for a plurality of third recognition results with a highest confidence; and a marking sub-module, configured to mark corresponding training pictures in the second training set by using the third recognition results.

Optionally, the second recognition results are used for indicating a probability that the recognized pathological feature (that is, the image feature) belongs to each of a plurality of pathological types, and the searching sub-module may be further configured to:

calculate a confidence s of a second recognition result of a current training picture in the second training set according to the following formula:

$$s = u * d^{w_1} + w_2 * v$$

u being a parameter that is used for representing importance of the current training picture and that is determined according to a probability of each type in the second recognition result of the current training picture, d being a density parameter determined according to a feature vector recognized by the third neural network model from the current training picture and a feature vector of the training pictures in the second training set, v being a diversity parameter determined according to the feature vector recognized by the third neural network model from the current training picture and a feature vector of the training pictures in the first training set, $w_1$ and $w_2$ being pre-configured parameters; and obtain a plurality of results with a highest confidence in all the second recognition results of the training pictures in the second training set as third recognition results.

Optionally, the return unit is configured to return the first recognition result used for representing the pathological type of a recognized image feature and a confidence of the image feature belonging to the pathological type.

Optionally, the return unit is further configured to return a first recognition result used for representing the NPDR; and/or return a first recognition result used for representing PDR.

If a DR fundus image classification model (that is, the first neural network model) is trained by using a supervised learning method, the following defects may be caused:

(1) Performance of the DR classification model depends on a scale of data manually marked, and a classification model with high quality needs to be trained by using a large scale of marked data;

(2) That marking personnel may add newly marked data in a process of training is not considered in the training method of the DR classification model, and only a scenario of performing one-time training in an unchanged training set is considered.

(3) The DR classification model is in short of a mechanism of automatically selecting and providing high-quality and unmarked data for the marking personnel to generate newly training data.

However, in the embodiments of this application, a large quantity of manually marked data with known classification does not need to be used as training samples, data that enables the model to converge at a higher speed can be marked through automatic and purposeful selection, and is used for training of a next stage. By using such a method, a quantity of marked data needed before convergence of model training can be reduced greatly, which effectively reduces the costs caused by manually marking data during training, thereby training a high-quality model with the least marked data.

Examples and application scenarios in which the foregoing modules are the same as those of the corresponding steps, but are not limited to the content disclosed in the foregoing embodiments. The foregoing modules may be run in the hardware environment shown in FIG. 1 as a part of the apparatus, and may be implemented by software, or may be implemented by hardware. The hardware environment includes a network environment.

According to another aspect of the embodiments of this application, a server or a terminal configured to implement the foregoing image feature recognition method is further provided.

Figure 10:
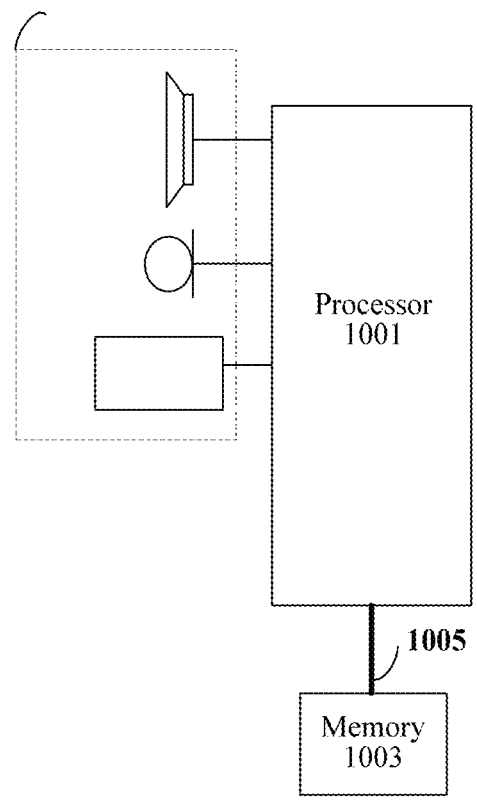
FIG. 10 is a structural block diagram of a server according to an embodiment of this application.

FIG. 10 is a structural block diagram of a server according to an embodiment of this application. As shown in FIG. 10, the server may include: one or more (only one is shown in FIG. 10) processor 1001, a memory 1003, and a transmission apparatus 1005 (such as the transmitting apparatus in the foregoing embodiments). As shown in FIG. 10, the server may further include an input/output device 1007.

The memory 1003 may be configured to store a software program and a module, for example, a program instruction/ module corresponding to the image feature recognition method and apparatus in an embodiment of this application, and the processor 1001 performs various functional applications and data processing by running a software program and a module stored in the memory 1003, that is, implementing the foregoing image feature recognition method. The memory 1003 may include a high-speed random memory, and may further include a non-volatile memory such as one or more magnetic storage apparatuses, a flash, or another non-volatile solid-state memory. In some examples, the memory 1003 may further include memories disposed remote to the processor 1001, and these remote memories may be connected to the server through a network. Instances of the network include, but are not limited to, the Internet, an intranet, a local area network, a mobile communications network, and a combination thereof.

The transmission apparatus 1005 is configured to receive or send data by means of a network, or may further be configured to transmit data between the processor and the memory. Optional examples of the foregoing network may include a wired network and a wireless network. In an example, the transmission apparatus 1005 includes a network interface controller (NIC). The NIC may be connected to another network device and a router by using a network cable, so as to communicate with the Internet or the local network. In an example, the transmission apparatus 1005 is a radio frequency (RF) module, which communicates with the Internet in a wireless manner.

Optionally, the memory 1003 is configured to store an application program.

The processor 1001 may invoke, by using the transmission apparatus 1005, the application program stored in the memory 1003, to perform the following steps:

obtaining a recognition request, the recognition request being used for requesting to recognize an image feature in a target picture;

recognizing the image feature in the target picture by using a first neural network model, the first neural network model being obtained by training a parameter in a second neural network model by using a first training set and a second training set, image features of training pictures in the first training set being marked, and image features of training pictures in the second training set being not marked; the first neural network model trained by the first training set being used for recognizing the image features of the training pictures in the second training set, and the training pictures with the image features recognized in the second training set being used for continuing to train the first neural network model; and returning a first recognition result of the first neural network model, the first recognition result being used for at least indicating the image feature recognized from the target picture.

The processor 1001 is further configured to perform the following steps performing training initialization on the parameter in the second neural network model by using the training pictures in the first training set, and using the second neural network model after the parameter initialization as a third neural network model;

recognizing, the image features of the training pictures in the second training set by using the third neural network model, and marking the training pictures in the second training set by using second recognition results of the third neural network model, the second recognition results being used for at least indicating the image features recognized from the training pictures in the second training set; and re-adjusting a parameter in the third neural network model by continuing to train the third neural network model by using the marked training pictures in the second training set, and using the third neural network model after the parameter re-adjustment as the first neural network model.

In this embodiment of this application, the image feature of the target picture is recognized by using the first neural network model when the recognition request is obtained, and a first recognition result of the first neural network model is returned, the first recognition result being used for at least indicating the image feature recognized from the target picture. The foregoing neural network model may exist in a computer device in a form of software, and rapidly show a recognition result. If a to-be-recognized image feature (for example, a pathological feature) is DR, a technical problem of low efficiency of screening for DR in the related art may be resolved, thereby improving efficiency of screening for DR.

Optionally, for an optional example in this embodiment, reference may be made to the examples described in the foregoing embodiments, and details are not repeated herein.

A person of ordinary skill in the art may understand that the structure shown in FIG. 10 is merely an example, and the server may be a server device such as a smartphone (for example, an Android mobile phone and an iOS mobile phone), a tablet computer, a palmtop computer, mobile Internet devices (MID), and a PAD. FIG. 10 does not limit the structure of the foregoing electronic apparatus. For example, the server may further include more or less components (for example, a network interface and a display apparatus) than those shown in FIG. 10, or have configuration different with that shown in FIG. 10.

A person of ordinary skill in the art may understand that all or a part of the steps of the methods of the foregoing embodiments may be implemented by a program instructing relevant hardware of a server device. The program may be stored in a computer readable storage medium. The storage medium may include a flash disk, a read-only memory (ROM), a random access memory (RAM), a magnetic disk, a compact disc, or the like.

An embodiment of this application further provides a storage medium. Optionally, in this embodiment, the storage medium may be configured to store program code for performing the image feature recognition method.

Optionally, in this embodiment, the storage medium may be located in at least one of a plurality of network devices in a network shown in the foregoing embodiment.

Optionally, in this embodiment, the storage medium is configured to store program code used for performing the following steps:

S41: Obtain a recognition request, the recognition request being used for requesting to recognize an image feature in a target picture.

S42: Recognize the image feature in the target picture by using a first neural network model, the first neural network model being obtained by training a parameter in a second neural network model by using a first training set and a second training set, image features of training pictures in the first training set being marked, and image features of training pictures in the second training set being not marked; the first neural network model trained by the first training set being used for recognizing the image features of the training pictures in the second training set, and the training pictures with the image features recognized in the second training set being used for continuing to train the first neural network model.

S43: Return a first recognition result of the first neural network model, the first recognition result being used for at least indicating the image feature recognized from the target picture.

Optionally, the storage medium is further configured to store program code for performing the following steps:

S51: Perform training initialization on the parameter in the second neural network model by using the training pictures in the first training set, and use the second neural network model after the parameter initialization as a third neural network model.

S52: Recognize, the image features of the training pictures in the second training set by using the third neural network model, and mark the training pictures in the second training set by using second recognition results of the third neural network model, the second recognition results being used for at least indicating the image features recognized from the training pictures in the second training set.

S53: Re-adjust a parameter in the third neural network model by continuing to train the third neural network model by using the marked training pictures in the second training set, and use the third neural network model after the parameter re-adjustment as the first neural network model.

Optionally, for an optional example in this embodiment, reference may be made to the examples described in the foregoing embodiments, and details are not repeated herein.

Optionally, in this embodiment, the storage medium may include, but is not limited to, various media such as a USB flash drive, a read-only memory (ROM), a random access memory (RAM), a removable hard disk, a magnetic disk, and an optical disc that can store the program code.

The sequence numbers of the foregoing embodiments of this application are merely for description purpose and do not indicate the preference of the embodiments.

When the integrated unit in the foregoing embodiments is implemented in the form of a software function unit and sold or used as an independent product, the integrated unit may be stored in the foregoing computer-readable storage medium. Based on such understanding, the technical solutions of this application essentially, or some contributing to the related art, or all or some of the technical solutions may be implemented in a form of a software product. The computer software product is stored in a storage medium and includes several instructions for instructing one or more computer devices (which may be a personal computer, a server, a network device, or the like) to perform all or some of steps of the methods in the embodiments of this application.

In the foregoing embodiments of this application, descriptions of the embodiments have different emphases, and as for parts that are not described in detail in one embodiment, reference can be made to the relevant descriptions of the other embodiments.

In the several embodiments provided in this application, it is understood that the disclosed client may be implemented in other manners. The apparatus embodiments described above are merely exemplary. For example, the division of the units is merely the division of logic functions, and may use other division manners during actual implementation. For example, a plurality of units or components may be combined, or may be integrated into another system, or some features may be omitted or not performed. In addition, the coupling, or direct coupling, or communication connection between the displayed or discussed components may be the indirect coupling or communication connection by means of some interfaces, units, or modules, and may be electrical or of other forms.

The units described as separate parts may or may not be physically separate, and parts displayed as units may or may not be physical units, may be located in one position, or may be distributed on a plurality of network units. Some or all of the units may be selected according to actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in the form of hardware, or may be implemented in the form of software functional unit.

The above descriptions are merely optional implementations of this application, and a person of ordinary skill in the art can make various improvements and refinements without departing from the spirit of this application. All such modifications and refinements are also be intended to be covered by this application.

INDUSTRIAL APPLICABILITY

In the embodiments, a server obtains a recognition request, the recognition request being used for requesting to recognize an image feature in a target picture; the server recognizes the image feature in the target picture by using a first neural network model, the first neural network model being obtained by training a parameter in a second neural network model by using a first training set and a second training set, image features of training pictures in the first training set being marked, and image features of training pictures in the second training set being not marked, the first neural network model trained by the first training set being used for recognizing the image features of the training pictures in the second training set, and the training pictures with the image features recognized in the second training set being used for continuing to train the first neural network model; and the server returns a first recognition result of the first neural network model, the first recognition result being used for at least indicating the image feature recognized from the target picture. A technical problem of relatively low efficiency of screening for DR in the related art is resolved, thereby improving the screening efficiency of the DR.

What is claimed is:

1. An image feature recognition method, comprising:
obtaining, by a computing device, a first training set and a second neural network model, wherein image features of training pictures in the first training set are marked and the second neural network model includes parameters to be trained;
training, by the computing device, the parameters of the second neural network model into a first neural network model using the marked image features of training pictures in the first training set that have been marked;
applying, by the computing device, a second training set to the first neural network model, wherein image features of training pictures in the second training set are not marked, to recognize image features of a subset of the training pictures in the second training set;
marking, by the computing device, the recognized image features of the subset of the training pictures in the second training set accordingly, further including indicating the image features recognized from the training pictures in the second training set using second recognition results of a third neural network model;
adjusting, by the computing device, a parameter in the third neural network model by continuing to train the third neural network model by using the marked training pictures in the second training set, and using the third neural network model after the parameter adjustment as the first neural network model, wherein the second recognition results are used for at least indicating the image features recognized from the training pictures in the second training set and for indicating a probability that the recognized image feature belongs to each of a plurality of pathological types;
calculating, by the computing device, a confidence of a second recognition result of a current training picture in the second training set based on (i) a parameter that is used for representing importance of the current training picture; (ii) a density parameter determined according to a feature vector recognized by the third neural network model from the current training picture and a feature vector of the training pictures in the second training set and (iii) a diversity parameter determined according to the feature vector recognized by the third neural network model from the current training picture and a feature vector of the training pictures in the first training set; and
updating, by the computing device, parameters of the first neural network model using the image features of the subset of the training pictures in the second training set that have been marked.

2. The method according to claim 1, further comprising:
before training, by the computing device, the parameters of the second neural network model:
performing, by the computing device, training initialization on the parameters of the second neural network model by using the training pictures in the first training set, and using the second neural network model after the parameter initialization as a third neural network model; and
wherein the applying, by the computing device, the second training set to the first neural network model further comprises:
recognizing, by the computing device, the image features of the training pictures in the second training set by using the third neural network model.

3. The method according to claim 2, wherein the marking, by the computing device, the training pictures in the second training set by using second recognition results of the third neural network model comprises:
searching, by the computing device, all second recognition results of the training picture in the second training set for a plurality of third recognition results with a highest confidence; and
marking, by the computing device, corresponding training pictures in the second training set by using the third recognition results.

4. The method according to claim 3, wherein the searching, by the computing device, all second recognition results of the training picture in the second training set for a plurality of third recognition results with a highest confidence comprises:
calculating, by the computing device, the confidence s of the second recognition result of the current training picture in the second training set according to the following formula:

$$s = PA * d^{w_1} + w_2 * v$$

PA is the parameter that is used for representing importance of the current training picture and that is determined according to a probability of each type in the second recognition result of the current training picture, d being the density parameter determined according to the feature vector recognized by the third neural network model from the current training picture and the feature vector of the training pictures in the second training set, v being the diversity parameter determined according to the feature vector recognized by the third neural network model from the current training picture and the feature vector of the training pictures in the first training set, $w_1$ and $w_2$ being pre-configured parameters; and obtaining, by the computing device, a plurality of results with a highest confidence in all the second recognition results of the training pictures in the second training set as the third recognition results.

5. The method according to claim 1, further comprising:
obtaining, by the computing device, a recognition request for recognizing an image feature in a target picture;
applying, by the computing device, the target picture to the first neural network model; and
returning, by the computing device, a first recognition result from the first neural network model, the first recognition result including at least one indicator of the image feature recognized from the target picture.

6. The method according to claim 5, wherein the image feature comprises a pathological feature, and the returning, by the computing device, a first recognition result of the first neural network model comprises:
returning, by the computing device, the first recognition result used for representing a pathological type of a recognized pathological feature and a confidence that the pathological feature belongs to the pathological type.

7. The method according to claim 5, wherein the image feature comprises a pathological feature, and the returning, by the computing device, a first recognition result of the first neural network model comprises:
returning, by the computing device, the first recognition result used for representing a non-proliferative diabetic retinopathy; and/or
returning, by the computing device, the first recognition result used for representing a proliferative diabetic retinopathy.

8. A computing device, comprising one or more processors and one or more memories storing program units that, when executed by the one or more processors, cause the computing device to perform a plurality of operations including:
obtaining, by the computing device, a first training set and a second neural network model, wherein image features of training pictures in the first training set are marked and the second neural network model includes parameters to be trained;
training, by the computing device, the parameters of the second neural network model into a first neural network model using the marked image features of training pictures in the first training set that have been marked;
applying, by the computing device, a second training set to the first neural network model, wherein image features of training pictures in the second training set are not marked, to recognize image features of a subset of the training pictures in the second training set;
marking, by the computing device, the recognized image features of the subset of the training pictures in the second training set accordingly, further including indicating the image features recognized from the training pictures in the second training set using second recognition results of a third neural network model;

adjusting, by the computing device, a parameter in the third neural network model by continuing to train the third neural network model by using the marked training pictures in the second training set, and using the third neural network model after the parameter adjustment as the first neural network model, wherein the second recognition results are used for at least indicating the image features recognized from the training pictures in the second training set and for indicating a probability that the recognized image feature belongs to each of a plurality of pathological types;
calculating, by the computing device, a confidence of a second recognition result of a current training picture in the second training set based on (i) a parameter that is used for representing importance of the current training picture; (ii) a density parameter determined according to a feature vector recognized by the third neural network model from the current training picture and a feature vector of the training pictures in the second training set and (iii) a diversity parameter determined according to the feature vector recognized by the third neural network model from the current training picture and a feature vector of the training pictures in the first training set; and
updating, by the computing device, parameters of the first neural network model using the image features of the subset of the training pictures in the second training set that have been marked.

9. The computing device according to claim 8, wherein the plurality of operations further comprise:
before training, by the computing device, the parameters of the second neural network model:
performing, by the computing device, training initialization on the parameters of the second neural network model by using the training pictures in the first training set, and using the second neural network model after the parameter initialization as a third neural network model; and
wherein the applying, by the computing device, the second training set to the first neural network model further comprises:
recognizing, by the computing device, the image features of the training pictures in the second training set by using the third neural network model.

10. The computing device according to claim 9, wherein the marking, by the computing device, the training pictures in the second training set by using second recognition results of the third neural network model comprises:
searching, by the computing device, all second recognition results of the training picture in the second training set for a plurality of third recognition results with a highest confidence; and
marking, by the computing device, corresponding training pictures in the second training set by using the third recognition results.

11. The computing device according to claim 10, wherein the searching, by the computing device, all second recognition results of the training picture in the second training set for a plurality of third recognition results with a highest confidence comprises:
calculating, by the computing device, the confidence s of the second recognition result of the current training picture in the second training set according to the following formula:

$$s = PA * d^{w_1} + w_2 * v$$

PA is the parameter that is used for representing importance of the current training picture and that is determined according to a probability of each type in the second recognition result of the current training picture, d being the density parameter determined according to the feature vector recognized by the third neural network model from the current training picture and the feature vector of the training pictures in the second training set, v being the diversity parameter determined according to the feature vector recognized by the third neural network model from the current training picture and the feature vector of the training pictures in the first training set, $w_1$ and $w_2$ being pre-configured parameters; and obtaining, by the computing device, a plurality of results with a highest confidence in all the second recognition results of the training pictures in the second training set as the third recognition results.

12. The computing device according to claim 8, wherein the plurality of operations further comprise:
  obtaining, by the computing device, a recognition request for recognizing an image feature in a target picture;
  applying, by the computing device, the target picture to the first neural network model; and
  returning, by the computing device, a first recognition result from the first neural network model, the first recognition result including at least one indicator of the image feature recognized from the target picture.

13. The computing device according to claim 12, wherein the image feature comprises a pathological feature, and the returning, by the computing device, a first recognition result of the first neural network model comprises:
  returning, by the computing device, the first recognition result used for representing a pathological type of a recognized pathological feature and a confidence that the pathological feature belongs to the pathological type.

14. The computing device according to claim 12, wherein the image feature comprises a pathological feature, and the returning, by the computing device, a first recognition result of the first neural network model comprises:
  returning, by the computing device, the first recognition result used for representing a non-proliferative diabetic retinopathy; and/or
  returning, by the computing device, the first recognition result used for representing a proliferative diabetic retinopathy.

15. A non-transitory computer readable storage medium, storing a plurality of program units that, when executed by a computing device having one or more processors, cause the computing device to perform a plurality of operations including:
  obtaining, by the computing device, a first training set and a second neural network model, wherein image features of training pictures in the first training set are marked and the second neural network model includes parameters to be trained;
  training, by the computing device, the parameters of the second neural network model into a first neural network model using the marked image features of training pictures in the first training set that have been marked;
  applying, by the computing device, a second training set to the first neural network model, wherein image features of training pictures in the second training set are not marked, to recognize image features of a subset of the training pictures in the second training set;
  marking, by the computing device, the recognized image features of the subset of the training pictures in the second training set accordingly, further including indicating the image features recognized from the training pictures in the second training set using second recognition results of a third neural network model,
  adjusting, by the computing device, a parameter in the third neural network model by continuing to train the third neural network model by using the marked training pictures in the second training set, and using the third neural network model after the parameter adjustment as the first neural network model, wherein the second recognition results are used for at least indicating the image features recognized from the training pictures in the second training set and for indicating a probability that the recognized image feature belongs to each of a plurality of pathological types;
  calculating, by the computing device, a confidence of a second recognition result of a current training picture in the second training set based on (i) a parameter that is used for representing importance of the current training picture; (ii) a density parameter determined according to a feature vector recognized by the third neural network model from the current training picture and a feature vector of the training pictures in the second training set and (iii) a diversity parameter determined according to the feature vector recognized by the third neural network model from the current training picture and a feature vector of the training pictures in the first training set; and
  updating, by the computing device, parameters of the first neural network model using the image features of the subset of the training pictures in the second training set that have been marked.

16. The non-transitory computer readable storage medium according to claim 15, wherein the plurality of operations further comprise:
  before training, by the computing device, the parameters of the second neural network model:
  performing, by the computing device, training initialization on the parameters of the second neural network model by using the training pictures in the first training set, and using the second neural network model after the parameter initialization as a third neural network model; and
  wherein the applying, by the computing device, the second training set to the first neural network model further comprises:
    recognizing, by the computing device, the image features of the training pictures in the second training set by using the third neural network model.

17. The non-transitory computer readable storage medium according to claim 16, wherein the marking, by the computing device, the training pictures in the second training set by using second recognition results of the third neural network model comprises:
  searching, by the computing device, all second recognition results of the training picture in the second training set for a plurality of third recognition results with a highest confidence; and
  marking, by the computing device, corresponding training pictures in the second training set by using the third recognition results.

18. The non-transitory computer readable storage medium according to claim 17, wherein the searching, by the computing device, all second recognition results of the training picture in the second training set for a plurality of third recognition results with a highest confidence comprises:

calculating, by the computing device, the confidence s of the second recognition result of the current training picture in the second training set according to the following formula:

$$s = PA * d^{w_1} + w_2 * v$$

PA is the parameter that is used for representing importance of the current training picture and that is determined according to a probability of each type in the second recognition result of the current training picture, d being the density parameter determined according to the feature vector recognized by the third neural network model from the current training picture and the feature vector of the training pictures in the second training set, v being the diversity parameter determined according to the feature vector recognized by the third neural network model from the current training picture and the feature vector of the training pictures in the first training set, $w_1$ and $w_2$ being pre-configured parameters; and obtaining, by the computing device, a plurality of results with a highest confidence in all the second recognition results of the training pictures in the second training set as the third recognition results.

19. The non-transitory computer readable storage medium according to claim 15, wherein the plurality of operations further comprise:

obtaining, by the computing device, a recognition request for recognizing an image feature in a target picture;

applying, by the computing device, the target picture to the first neural network model; and returning, by the computing device, a first recognition result from the first neural network model, the first recognition result including at least one indicator of the image feature recognized from the target picture.

20. The non-transitory computer readable storage medium according to claim 19, wherein the image feature comprises a pathological feature, and the returning, by the computing device, a first recognition result of the first neural network model comprises:

returning, by the computing device, the first recognition result used for representing a pathological type of a recognized pathological feature and a confidence that the pathological feature belongs to the pathological type.

\* \* \* \* \*